United States Patent [19]

Simonovitch et al.

[11] 3,954,996

[45] May 4, 1976

[54] WATER-SOLUBLE COMPOSITION COMPRISING A ROBENIDINE SALT

[75] Inventors: Chaim Simonovitch, Rishon Le-Zion; Morris E. Stolar, Tel-Aviv, both of Israel

[73] Assignee: ABIC Ltd., Ramat-Gan, Israel

[22] Filed: July 15, 1974

[21] Appl. No.: 488,476

[30] Foreign Application Priority Data

July 20, 1973 Israel.................................... 42800

[52] U.S. Cl. ............................................... 424/326
[51] Int. Cl.$^2$ ....................................... A61K 31/155
[58] Field of Search .................................... 424/326

[56] References Cited
UNITED STATES PATENTS 3,769,432  10/1973  Tomcufcik ......................... 424/326

*Primary Examiner*—Sam Rosen
*Attorney, Agent, or Firm*—Steinberg and Blake

[57] ABSTRACT

There are disclosed water-soluble compositions comprising a 1,3-bis-[(p-chlorobenzylidene)-amino]-guanidine (called Robenidine) salt, particularly the hydrochloride. Said compositions comprise also a suitable water-soluble organic solvent and a suitable water-soluble solubilizer; the solvent and the solubilizer being miscible with each other. There are also disclosed aqueous solutions comprising the above composition and a method for the treatment of animals being infected with Cocciodiosis with said aqueous solution.

13 Claims, No Drawings

WATER-SOLUBLE COMPOSITION COMPRISING A ROBENIDINE SALT

The present invention relates to a water-soluble composition comprising a 1,3-bis-[(p-chlorobenzylidene)-amino] guanidine salt, hereinafter called Robenidine salt. The present invention will be in particular illustrated with reference to the hydrochloride but it is not restricted thereto.

It is known that Robenidine hydrochloride can be utilised in the treatment of warm blooded animals, in particular, fowl, infected with the protozoal disease Coccidiosis. See, for example, W. M. Reich et al., Avian diseases 14 (4) 142, (1971); S. Kantor et al., Science 168, 373–4 (1970); British Patent Specification No. 1.256.723; J. F. Ryley and R. G. Wilson, Z. Parazitenk 37, 85–93 (1971).

A veterinary medicine which has to be administered in a dose being as uniform as possible is admixed either with the food or with the drinking water. The preferred manner of administration is as part of the drinking water for the following reasons:

The administration of medicated feed to animals being sick is often unsatisfactory. In this state of health, the appetite of the animals is reduced, so that they swallow a lower amount of feed and as the result thereof a therapeutic dose of the medicine which is less than the required one. On the other hand animals being sick usually continue drinking water.

Moreover, it is known that warm-blooded animals drink about twice the amount they eat and thus about half the concentration of the drug required in the feed is required in water. In addition, the presence of a drug in a solution enhances curing because of better availability. Finally, the administration of a veterinary medicine for curing purposes in an aqueous solution has the advantage of being simpler and more convenient that the administration as part of the feed. In the first case the farmer or the veterinarian obtains a composition comprising the active material which composition can be readily mixed with water, while if he administers a medicated feed he is dependent on the supply from the feed manufacturer.

French Patent Specification No. 2.012.054 states that the various Robenidine salts are very soluble in water and hints that said salts can be administered as part of the drinking water.

The therapeutically effectful dose of Robenidine salts varies from animal to animal. Thus, for example, the recommended dose for fowl in feed is 30 mg per kg feed. It has now been found by the applicants that for complete cure about 15 mg per L of drinking water is desired in the treatment of fowl.

Applicants have tried to establish the solubility of some Robenidine salts in water at room temperature. They have found that after about ½ hour only 5 mg of the hydrochloride or of the nitrate were dissolved in 1 L of water. (Of the sulfate and the hydrobromide no traces could be found after ½ hour of stirring). Even after constant stirring for about 24 hours only about 8 mg of the hydrochloride or of the nitrate were dissolved in 1 L of water.

The above rate of solubility is certainly not sufficient in order to administer the Robenidine salt as part of the drinking water. The amount dissolved in water, even after 24 hours, is much below the therapeutic dose required. Moreover, in order that a drug may be administered as part of the drinking water it has to be instantaneously soluble in water.

It has thus been desirable to provide a water-soluble composition comprising a Robenidine salt, which composition should not be toxic, be physiologically acceptable, palatable, stable, storable and instantaneously miscible with water to yield an aqueous solution comprising therapeutically effective amounts of the drug. Said solution should remain free of any precipitate even if the pH of the water varies within the range allowed for drinking water. Moreover, such solution should be stable for at least 24 hours.

It has now surprisingly been found that when a suitable water-soluble organic solvent is admixed with a suitable water-soluble organic solubilizer and with a certain amount of a Robenidine salt, a composition is obtained which is instantenously soluble in water.

The present invention thus consists in a water-soluble composition comprising a Robenidine salt, a suitable water-soluble organic solvent and a suitable water-soluble solubilizer; the solvent and the solubilizer being miscible with each other.

The organic solvents should not be toxic and be physiologically acceptable. As suitable solvents there may be mentioned, for example, polyols and derivatives thereof, e.g. glycol, glycerol, propylene glycol, polyethylene glycols of various average molecular weights varying from 200–1540, polypropylene glycol, tetrahydrofurfuryl ethylene glycol ether and methylidene glycerol; dimethyl sulfoxide and dimethyl formamide.

The solubilizers too should not be toxic and be physiologically acceptable. As suitable solubilizers there may be mentioned, for example, non-ionic suface active agents, such as polyoxysorbitan fatty acids; polyoxyalkylene mono-, di- and tri-glycerides, e.g. polyoxyethylene glycerides; polyoxyalkylene sorbitol fatty acids, e.g. polyoxyethylene sorbitol fatty acids; polyoxyalkylene alkyl ethers; cationic surface active agents, such as quarternary ammonium salts, e.g. Bromosept (di-decyl dimethyl ammonium bromide); and anionic surface active agents, e.g. aryl alkyl sulfonates; Aerosol OT (sodium dioctyl sulfo succinate); etc.

The ratio solvent:solubilizer should be between 1:1 and 1:10 (parts by weight).

The ratio Robenidine salt:solvent-solubilizer mixture should be 0.1–5:99.9–95 (parts by weight).

The composition according to the present invention is prepared by mixing processes known per se.

The compositions according to the present invention may be used to prepare aqueous solutions containing upto 600 mg of a Robenidine salt, e.g. the hydrochloride, in 1 L of water. Said solutions are obtained instantenously at room temperature.

The present invention thus consists also in an aqueous solution of the composition according to the present invention containing a therapeutically effectful dose of a Robenidine salt.

The present invention relates also to a method for the treatment of annimals being infected with Cocciodiosis in which said animals drink an aqueous solution of the composition according to the present invention containing a therapeutically effectful dose of a Robenidine salt.

The present invention will now be illustrated with reference to the following Examples without being limited by same. All temperatures are indicated in degees centigrade.

EXAMPLE 1

1.5 g of finely pulverised Robenidine hydrochloride was added to 20 ml of propylene glycol and the mixture was stirred until a homogeneous paste was obtained. 200 ml of polyoxyethylene sorbitan monooletae (Tween 80) was then added and the mixture was stirred and heated to 70°. A clear viscous solution was obtained. After cooling to room temperature the solution was filtered.

The above composition when mixed with water yielded a clear, palatable and stable solution, For practical purposes 2–4 ml of the composition were used for 1 L of water.

The solution obtained was administered to groups of chicks (each group comprising 8 chicks) being infected at the age of 10 days with $10^6$ sporulated oocysts of E. Tenella. The chicks were weighed at the beginning of the experiment and after one week. The results are summarised in Table I.

Table I

|  | mg Rob. HCl/L | Average weight at the begin. | Average weight after 1 week | mortality | No. of oocysts left in the intestine |
|---|---|---|---|---|---|
|  | 15 | 78 g | 127 g | 0 | 0–1 |
|  | 12 | 83 g | 121 g | 0 | 0–2 |
|  | 10 | 77 g | 108 g | 1 | 0–1 |
| infected control | — | 79 g | 84 g | 0 | 3–10 |
| non infec. control | —. | 78 g | 106 g | — | — |

In order to test the solubility of the composition 8.4 ml thereof were dissolved in 100 ml of water, which corresponds to a concentration of 600 mg of Robenidine HCl in 1 L of water. A stable solution was obtained.

EXAMPLE 2

500 mg of finely pulverized Robenidine HCl was introduced to a previously melted 10 g of polyoxy ethylene triglyceride (Arlatone 289 - Atlas Corp.) The mixture was heated and stirred at 60°–80° until a fine paste was obtained. 66.6 ml of a solution prepared from 75 ml of polyethylene glycol (Carbowax 300) and 25 ml of propylene glycol was added and the mixture was stirred and heated at 60°–80° until a clear solution was obtained. After cooling to room temperature the solution was filtered. The solution had a concentration of 0.65 g of Robenidine HCl. 2.3 ml of said composition in 1 L of water yielded a concentration of 30 mg of Robenidine/ 1 L of water.

The aqueous solution was administered to groups to chicks (each group containing 8 chicks) infected at the age of 10 days with $10^6$ sporulated oocysts of E. Tenella. The chicks were weighed at the beginning of the experiment and after 1 week. The results are summarised in Table II.

Table II

|  | mg Rob. HCl/L | Average weight at the begin. | Average weight after 1 week | mortality | No. of oocysts left in the intestine |
|---|---|---|---|---|---|
|  | 30 | 79 g | 108 g | 0 | 0 |
|  | 15 | 78 g | 106 g | 2+ | 0 |
| infected control | — | 78 g | 84 g | 0 | 3–10 |
| non infec. control | — | 78 g | 106 g | 0 | — |

+death apparently not from Coccidiosis.

EXAMPLE 3

500 mg of finely pulverised Robenidine HCl was introduced to previously melted 5 g of Arlatone 285 Atlas Corp. and the mixture obtained was heated to 60°–80° until most of the salt was dissolved. 50 ml of a solution prepared from 75 ml of polyethylene glycol (Carbowax 300) and 25 ml of propylene glycol was added and the combined mixture was stirred and heated at 70°, until a clear solution was obtained. After cooling to room temperature the solution was filtered.

1.65 ml of the above solution when dissolved in 1 L of water yielded a concentration of 15 mg Robenidine HCl/1 L.

The aqueous solution obtained was administered to a group of chicks (each group comprising 8 chicks) infected at the age of 10 days with $10^6$ sporulated oocysts of E. Tenella. The chicks were weighed at the beginning of the experiment and again after 1 week. The results are summarised in Table III.

Table III

|  | mg Rob. HCl/L | Average weight at the begin. | Average weight after 1 week | mortality | No. of oocysts left in the intestine |
|---|---|---|---|---|---|
|  | 30 | 82 g | 115 g | 0 | 0 |
|  | 15 | 81 g | 112 g | 0 | 0 |
|  | 10 | 81 g | 114 g | 0 | 0 |
| infected control non infec. | — | 79 g | 84 g | 0 | 3–10 |

Table III-continued

| | mg Rob. HCl/L | Average weight at the begin. | Average weight after 1 week | mortality | No. of oocysts left in the intestine |
|---|---|---|---|---|---|
| control | — | 78 g | 106 g | 0 | 0 |

EXAMPLE 4

A composition as described in Example 3 was prepared, wherein the amount of Arlatone 285 utilised was 10 g.

1.2 ml of said composition was dissolved in 1 L of water. This corresponds to a concentration of 100 mg of Robenidine HCl in 1 L of water. A clear stable solution was obtained.

EXAMPLE 5

300 mg of Robenidine HCl was dissolved in 10 ml of dimethylsulfoxide (DMSO). 2 ml of a 50% ethanolic solution of Bromosept was added and the mixture obtained was stirred at room temperature until a clear solution was obtained.

0.6 ml of the above composition, comprising 15 mg of Rosenidine HCl, was dissolved in 1 L of water. The solution was administered to a group of chicks (each group comprising 8 chicks) infected at the age of 10 days with $10^6$ sporulated oocysts of E. Tenella. The chicks were weighed at the beginning of the experiment and after one week. The results are summarised in Table IV.

Table IV

| | mg Rob. HCl/L | Average weight at the begin. | Average weight after 1 week | mortality | No. of oocysts left in the intestine |
|---|---|---|---|---|---|
| | 15 | 78 g | 112 g | 0 | 0–1 |
| infected control | — | 79 g | 84 g | 0 | 3–10 |
| non infec. control | — | 78 g | 106 g | 0 | 0 |

EXAMPLE 6

100 mg of finely pulverised Robenidine HCl was added to 2 g of an alkyl aryl sulfonate (G-3300-Atlas Corp.) and the mixture obtained was stirred and heated to 60° until most of the salt was dissolved. The mixture obtained was added to 10 ml of a mixture composed of 7.5 ml of Carbowax 300 and 2.5 ml of propylene glycol. The mixture was heated at 70° until a clear solution was obtained. After cooling to room temperature the mixture was filtered.

2.4 ml of the above solution, comprising 20 mg of Robenidine HCl were dissolved in 1 L of water and yielded a clear stable solution.

When 6 ml of the above solution were dissolved in 1 L of water, a clear stable solution was also obtained.

EXAMPLE 7

100 mg of finely pulverised Robenidine HCl was added to 2 g of G-3634A (a quarternary ammonium derivative) (Atlas Corp.) and the mixture obtained was stirred and heated at 60° until most of the salt was dissolved. 10 ml of a mixture prepared from 7.5 ml of Carbowax 300 and 2.5 ml of propylene glycol was added and the mixture was stirred and heated at 70° until a clear solution was obtained. After cooling at room temperature the mixture was filtered.

2.4 ml of the above solution, comprising 20 mg of Robenidine HCl when dissolved in 1 L of drinking water gave a clear stable solution.

EXAMPLE 8

100 mg of Robenidine HCl was introduced into 10 ml of a solution prepared from 7.5 ml of Carbowax 300 and 2.5 ml of propylene glycol. The mixture obtained was stirred and heated at 70° until a clear solution was obtained. After cooling 10 ml of a 70% w/v of Aerosol OT (Atlas Corp.) was added and after short stirring a clear solution was obtained.

4 ml of the above solution was dissolved in 1 L of water and gave a clear solution comprising 20 mg of Robenidine HCl.

EXAMPLE 9

100 mg of Robenidine HBr was mixed with 2 g of Arlatone 285 and the mixture obtained was heated and stirred at 70° until all the salt was dissolved. 10 ml of a solution prepared from 7.5 ml of Carbowax 300 and 2.5 ml of propylene glycol was added and the mixture was heated to 70° until all the solids dissolved. The mixture was cooled to room temperature and filtered.

6.7 ml of the above solution, comprising approx. 60 mg of Robenidine HBr, were dissolved in 1 L of water and gave a clear stable solution.

EXAMPLE 10

100 mg of Robenidine nitrate were admixed in the same manner as described in Example 9 with 2 g of Arlatone (polyoxyethylene fatty glyceride produced by Atlas) 285 and 10 ml of the same mixture of Carbowax 300 and propylene glycol.

0.7 mg of the composition were dissolved in 100 ml of water, corresponding to approx. 60 mg Robenidine HBr in 1 L of water. A stable solution was obtained.

EXAMPLE 11

256 mg of Robenidine HCl was added to 33.5 g of propylene glycel and the mixture was stirred until aa homogenous paste was obtained. 33.5 g of Tween 80 was than added and the mixture was stirred and heated to 70°. A clear viscous solution was obtained, which was diluted with a sufficient amount of distilled water to yield 100 ml.

The above solution can be used in a proportional pump in a ratio of 1:128 yielding an aqueous solution comprising 20 mg of Robenidine in 1 L of water.

We claim:

1. A water-soluble composition comprising a physiologically acceptable salt of 1,3-bis([(p-chlorobenzylidine)-amino] quanidine, a physiologically acceptable water-soluble organic solvent in which said salt is soluble and a physiologically acceptable water-soluble surface active agent which acts as solubilizer for said salt and solvent in water, said solvent and said solubilizer being miscible with each other the ratio by weight of solvent to solubilizer being between about 1:1 and 1:10 and the ratio by weight of salt to solvent plus solubilizer being between about 0.1–5:99.9–95.

2. A composition according to claim 1, wherein said salt is selected from the group consisting of the hydrochloride, the hydrobromide and the nitrate.

3. A composition according to claim 1, wherein said solvent is selected among the group consisting of glycol, glycerol, propylene glycol, polyethylene glycols of molecular weights of from 200–1540, water soluble polypropylene glycol, tetraglycol, glycerol formal, dimethyl sulfoxide and dimethyl formamide.

4. A composition according to claim 1, wherein said solubilizer is a non-ionic surface active agent.

5. A composition according to claim 4, wherein said solubilizer is selected among the group consisting of polyoxysorbitan fatty acids; polyoxyalkylene mono-, di- and tri-glycerides; polyoxyalkylene sorbitol fatty acids and polyalkylene alkyl ethers.

6. A composition according to claim 1, wherein said solubilizer is a cationic surface active agent.

7. A composition according to claim 6, wherein said solubilizer is a quaternary ammonium salt.

8. A composition according to claim 1, wherein said solubilizer is an anionic surface active agent.

9. A composition according to claim 8, wherein said solubilizer is an aryl alkyl sulfonate.

10. An aqueous solution comprising the composition claim 1 dissolved in water.

11. An aqueous solution according to claim 10, in which said salt is present in an amount of up to 600 mg. of salt per liter of water.

12. An aqueous solution according to claim 11, in which said salt is present in an amount of 100 to 600 mg. of salt per liter of water.

13. A method for the treatment of an animal infected with Cocciodiosis, which comprises causing said animal to drink an aqueous solution according to claim 10.

* * * * *